US005145640A

United States Patent [19]

Levin

[11] Patent Number: 5,145,640

[45] Date of Patent: Sep. 8, 1992

[54] METHOD FOR ACCELERATION OF LIQUID AND BULK MATERIALS AND APPARATUS FOR REALIZATION THEREOF

[76] Inventor: Igor A. Levin, Petro-zavodskaya ulitsa, 15, korpus 1, kv. 113, Moscow, U.S.S.R.

[21] Appl. No.: 635,562

[22] PCT Filed: Feb. 14, 1990

[86] PCT No.: PCT/SU90/00042

§ 371 Date: Dec. 26, 1990

§ 102(e) Date: Dec. 26, 1990

[87] PCT Pub. No.: WO90/11840

PCT Pub. Date: Oct. 18, 1990

[30] Foreign Application Priority Data

Apr. 4, 1989 [SU] U.S.S.R. .............................. 4666633

[51] Int. Cl.[5] .......................... A61L 2/00; B01F 11/02; F26B 9/00; B08B 7/02

[52] U.S. Cl. ...................................... 422/22; 422/291; 422/1; 34/164; 366/127; 210/748; 134/1

[58] Field of Search ............................ 422/22, 1, 291; 34/164 X; 366/110, 127 X; 210/748 X; 134/1

[56] References Cited

U.S. PATENT DOCUMENTS

| | | | |
|---|---|---|---|
| 1,945,015 | 1/1984 | Wurzbach et al. | 366/127 |
| 2,964,581 | 12/1960 | Hanff | 366/127 |
| 3,088,220 | 5/1963 | Ofner | 34/164 |
| 3,771,772 | 11/1973 | Honda | 366/110 |
| 3,830,099 | 8/1974 | Ichikawa | 366/127 |
| 4,556,467 | 12/1985 | Kuhn et al. | 204/193 |
| 4,834,124 | 5/1989 | Honda | 134/184 |
| 4,836,684 | 6/1989 | Javorik et al. | 366/114 |

*Primary Examiner*—Robert J. Warden
*Assistant Examiner*—T. A. Trembley
*Attorney, Agent, or Firm*—Burgess, Ryan & Wayne

[57] ABSTRACT

The method for acceleration of liquid and bulk materials comprises conversion of energy of the electromagnetic pulse of a radiator (1) into mechanical energy applied to the treated material by a plate element (3) of a conducting material having at least one degree of freedom in the direction of acceleration. The opposite surfaces of the place element (3) at the moment of emission of the electromagnetic pulse are brought in physical contact with the radiator and treated material, respectively.

An apparatus for realization of the above method comprises a radiator (1) connected with a source (2) of electromagnetic pulses, a plate element (3) of a conducting material arranged loosely on the radiator (1), the surface of said element being intended for placement of the treated material.

9 Claims, 4 Drawing Sheets

METHOD FOR ACCELERATION OF LIQUID AND BULK MATERIALS AND APPARATUS FOR REALIZATION THEREOF

Technical Field

The present invention relates to a method for acceleration of liquid and bulk materials and an apparatus for car-;ing out the method.

Prior Art

Widely known nowadays is the use of acceleration for treating various materials by centrifuging. In this method the acceleration produced are limited by the structural elements of the centrifuge (drive, shaft supports, etc.). Besides, acceleration of the material in the centrifuge basket takes a certain time. Thus, on the one hand, the treatment intensity is restricted by the limited value of acceleration and, on the other hand, productivity is rather low due to the necessity for accelerating and retarding the centrifuge.

There is also a method for treating liquid and bulk materials wherein the treated material is accelerated by electromagnetic pulses. For this purpose the treated material is placed into a container and the pulses are applied to the container bottom. This produces elastic deformation in the bottom so that the particles of the treated material are accelerated and start moving relative to one another (SU, A, 775559).

A disadvantage of such a method is the considerable energy losses of the electromagnetic pulses required for elastic deformation of the container bottom. The obtained accelerations are extremely low (2-5 g) which denies the possibility of intensifying the process of treatment.

Brief Description of the Invention

The object of the present invention is to provide a method for acceleration of materials being treated wherein the electromagnetic energy is converted into mechanical energy with a minimum of unproductive losses and also to provide an apparatus for carrying out the method.

The objects are achieved by providing a method for acceleration of liquid and solid materials by converting the energy of the electromagnetic pulse of a radiator into mechanical energy applied to the treated material wherein, according to the invention, the energy of the electromagnetic pulse is converted into mechanical energy by a plate-like element an electrical conducting material possessing at least one degree of freedom in the preset direction of acceleration and wherein the opposite surfaces of the plate element at the moment of pulse emission by the radiator is in physical contact with the radiator and the material to be treated, respectively.

Though it is no wish of the author to give theoretical substantiation to the physical phenomenon observed in operation of the disclosed method for acceleration of liquid and bulk materials, it may be presumed that ultra-high accelerations (a few thousand "g") are obtained by inducing a secondary field in a plate element, said field interacting with the primary electromagnetic field of the pulse radiator which produced a high-energy mechanical pulse. The arrangement of the plate element with at least one degree of freedom in the preset direction of acceleration, eliminates the expenditure of electromagnetic energy of the pulse for elastic deformation of the material interposed between the radiator and the material to be treated.

The effect of the disclosed invention is quite unexpected. Thus, in the course of experiments the material weighing eight kg was thrown up 3–4 m high by an electromagnetic pulse energy of a few joules.

The material to be treated can be water flowing onto one surface of the plate element while the electromagnetic pulses are emitted in a continuous mode.

The method also can intensify the cooling process in, say, cooling towers and other heat-exchange apparatuses.

The material to be treated can be biological material to be sterilized.

In this method the biological material is placed on one surface of the plate element.

Materials can be mixed by the flows of directing the various materials to be mixed onto the surface of the plate element. The method increases the productivity and completeness of mixing.

It is preferred that the leading edge of the pulse should be defined by the pulse rise time amounting to 10–20% of pulse duration. This ensures the maximum energy capacity of the pulse resulting in a high acceleration due to a high intensity of the process of interaction between the primary and secondary fields in the power transmitting element.

The disclosed method is carried out with an apparatus comprising a source of electromagnetic pulses connected with a radiator; in accordance with the invention, said apparatus comprises a converter for converting the energy of the electromagnetic pulse of the radiator into mechanical energy, said converter comprising a plate element installed with at least one degree of freedom, one surface of said plate element being kept in physical contact with the electromagnetic pulse radiator while the other surface is in contact with the material being treated.

It is preferred that the disclosed apparatus comprises at least one additional plate element wherein said plate elements are set at an angle to each other and that each additional plate element has one surface in physical contact with a corresponding additional radiator. Such an apparatus can be utilized, e.g., for mixing various materials, for heat-and-mass exchange, etc.

It is preferred that the disclosed apparatus be provided with a reflector set at a distance from the surface of the plate element and arranged parallel with its surface intended to receive the material to be treated. Such an apparatus is noted for a high efficiency of crushing or finely dividing of the solid and liquid material, respectively.

Brief Description of the Drawings

The invention will be described by way of concrete, though not confining, examples of embodiments of the invention with reference to the accompanying drawings in which.

Best Mode to Carry out the Invention

In the description that follows the same elements are indicated by the same reference numbers.

Figure 1:
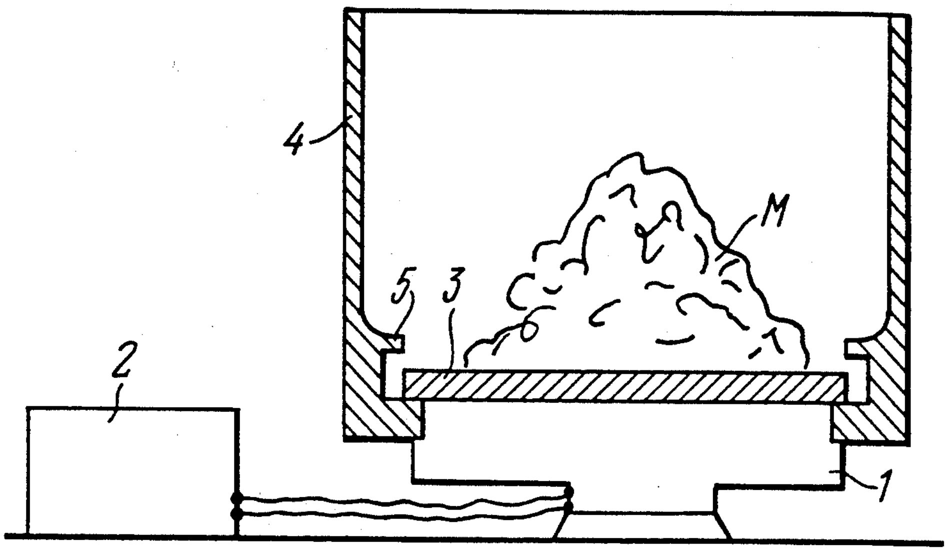
FIG. 1 is a schematic diagram of the apparatus for carrying out the method of the invention.

FIGS. 1 shows an apparatus for carrying out the disclosed method. The apparatus comprises an electromagnetic pulse radiator 1 connected to a source 2 (generator) of electromagnetic pulses. The electromagnetic pulse is converted into movement by a plate element 3 one surface of which is in contact with the radiator 2. A container defined by a wall 4 accommodates the treated material M which is in physical contact with the second surface of the plate element 3 at the moment of pulse emission. The material M may be in place on the surface of the plate element 3 or it may be delivered to the surface just before pulse emission through a conduit by a conveyer, etc. The plate element 3 is made of a conducting material, preferably copper or aluminuum. The plate is installed with at least one degree of freedom in the present direction of acceleration (in this case vertically upward) and its movement is restricted by stops 5 (FIG. 1).

As the pulse is generated by the source 2, the electromagnetic pulse emitted by the radiator 1 induces a secondary electromagnetic field in the plate element 3 and the resultant field creates a mechanical pulse directed perpendicular to the surface of the plate element 3. Practically all the energy is converted into movement of the particles of the treated material M because the loosely arranged plate element 3 is not deformed. The developed accelerations determined by the pulse energy and the mass of the treated material reach a few hundred or even thousand "g"'s thus ensuring a high intensity of treatment. Thus, in the course of drying, the moisture is separated by tremendous forces of inertia applied to each particle; besides, disintegration of heterogeneous particles may occur with concurrent separation of particles with different specific weights which is feasible only under the effect of ultra-high accelerations.

The leading edge of the pulse is determined by the pulse rise time which ranges from 10 to 20% of pulse duration. A pulse rise time of less than 10% of pulse duration is impracticable since it can involve destruction of the plate element 3 under excessively heavy inertia loads. When the pulse rise time exceeds 20% of pulse duration both the pulse energy and the obtained accelerations are reduced.

Figure 2:
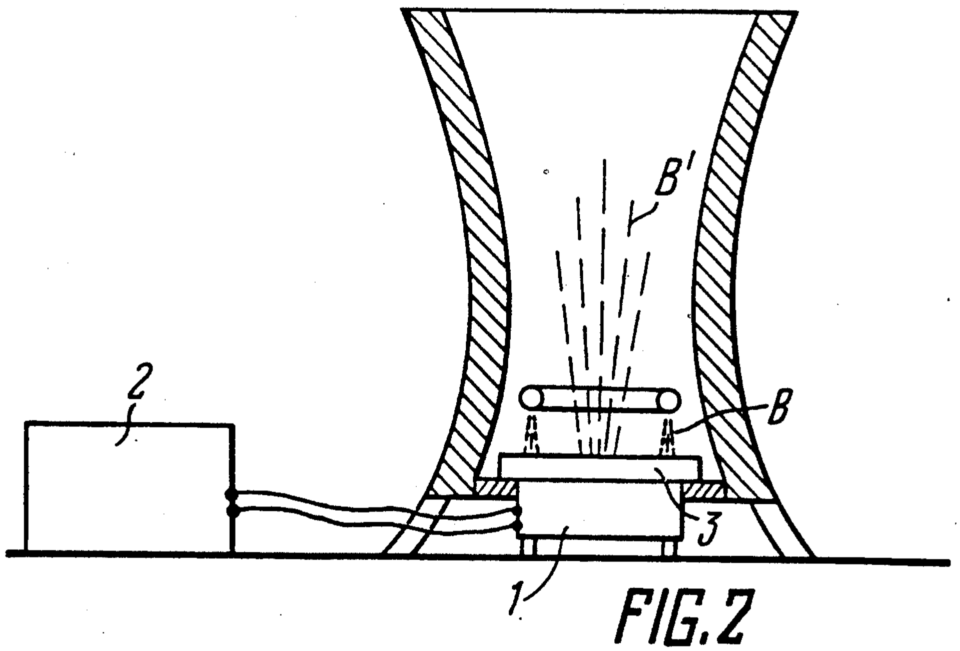
FIG. 2 illustrates a cooling tower in which water is cooled by the method according to the invention.

The treated material may be water or some other liquid whose flow B (FIG. 2) is directed onto one surface of the plate element 3 under the effect of electromagnetic pulses continuously emitted by the radiator 1. The wall 4 (FIG. 2) forms a cooling tower in which water is cooled with a higher intensity than in conventional cooling towers due to high accelerations. This permits reducing the amount of required circulating water.

Figure 3:
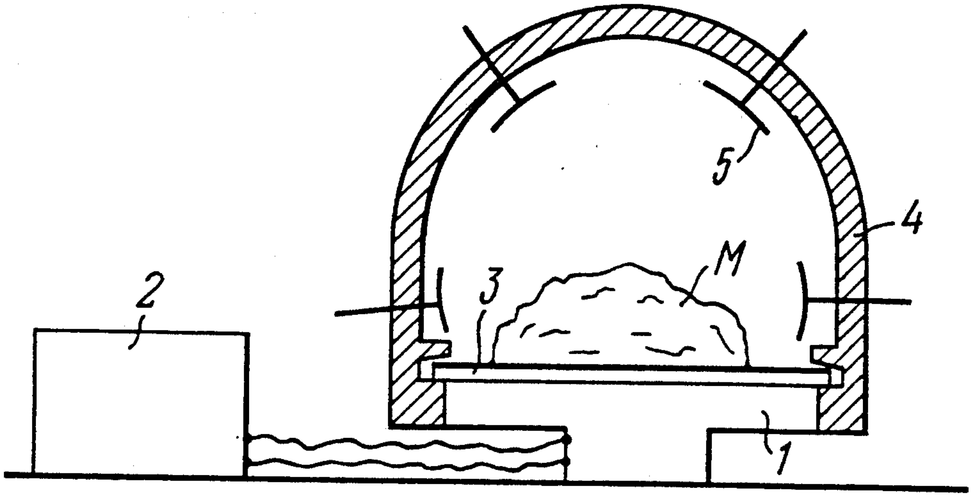
FIG. 3 illustrates a method for sterilization of a biological material according to the invention.

Shown in FIG. 3 is an apparatus wherein the disclosed method is used for sterilization of biological objects (any biological material for medical or food purposes, dressing materials with biological liquids, etc.). In addition, this apparatus comprises radiators 5 for thermal or ionizing radiation. This produces a combined effect on harmful microorganisms, viz., high acceleration and radiation.

Figure 4:
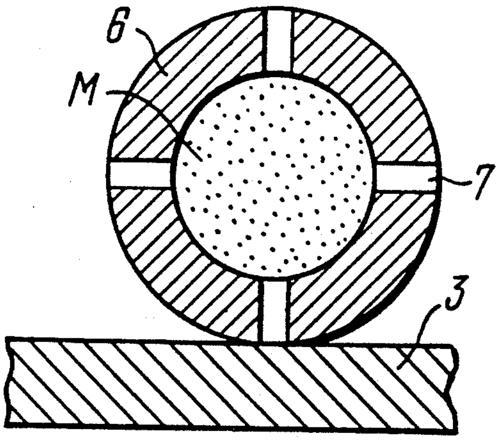
FIG. 4 illustrates a method for drying and compacting a material, according to the invention.

Shown in FIG. 4 is a method for drying and compaction by the use of a capsule 6 with perforations 7. The material M is placed into the capsule 6 which is installed on the plate element 3. When the pulse is emitted from the radiator (not shown in FIG. 4), the ultra-high acceleration causes intensive compression of material M in the capsule and squeezing out of moisture which is discharged through holes 7. This permits pelletizing the material.

Figure 5:
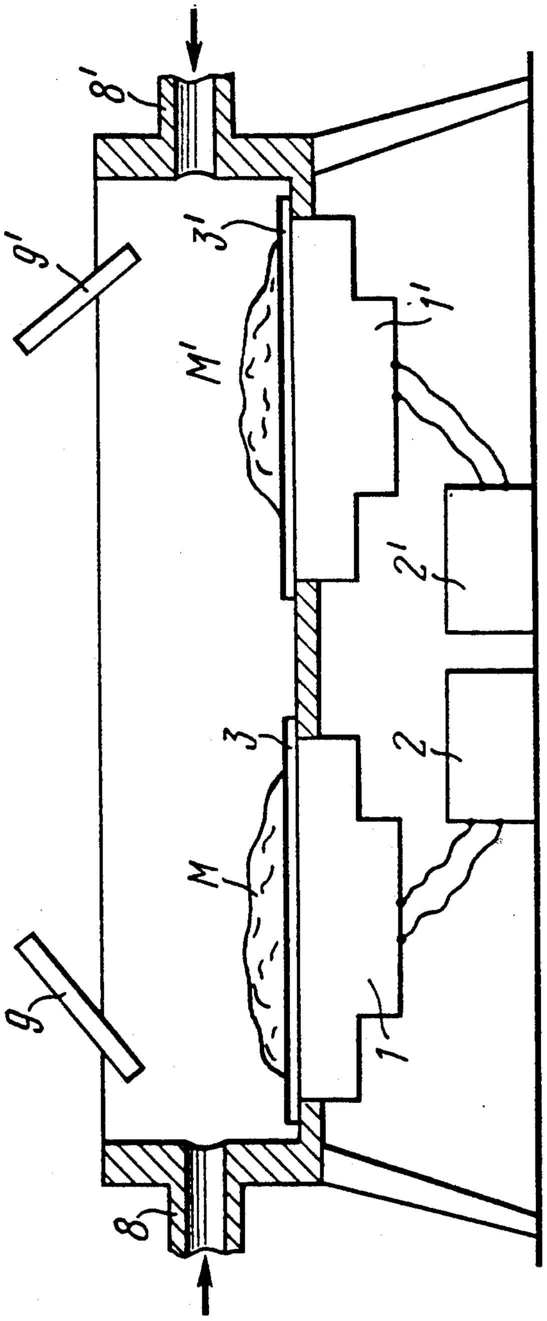
FIG. 5 illustrates a method for mixing various materials, according to the invention.

FIG. 5 illustrates the apparatus for mixing two different materials comprising identical sources 2, 2', radiators 1, 1' of electromagnetic pulses and plate elements 3, 3'. The materials M, M' are delivered through tubes 8, 8' while reflectors 9, 9' are arranged to face the plate elements 3, 3'. The emitted electromagnetic pulses accelerate the materials M, M' in a vertical direction then said pulses are reflected by reflectors 9, 9' and encounter high velocities causing their intensive mixing, heat exchange and mutual disintegration. This method can be utilized to obtain physical and chemical interaction of various materials.

Figure 6:
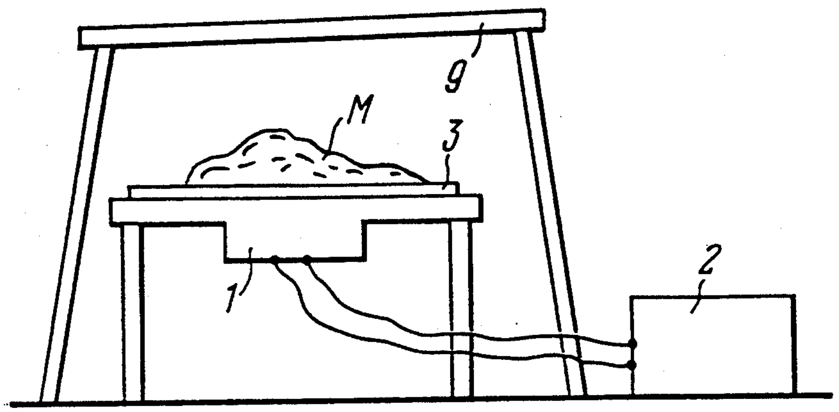
FIG. 6 illustrates an embodiment of an apparatus according to the invention.

The apparatus shown in FIG. 6 can be used as a version of the apparatus shown in FIG. 5 and is likewise provided with a reflector 9 for crushing the particles of material M.

Figure 7:
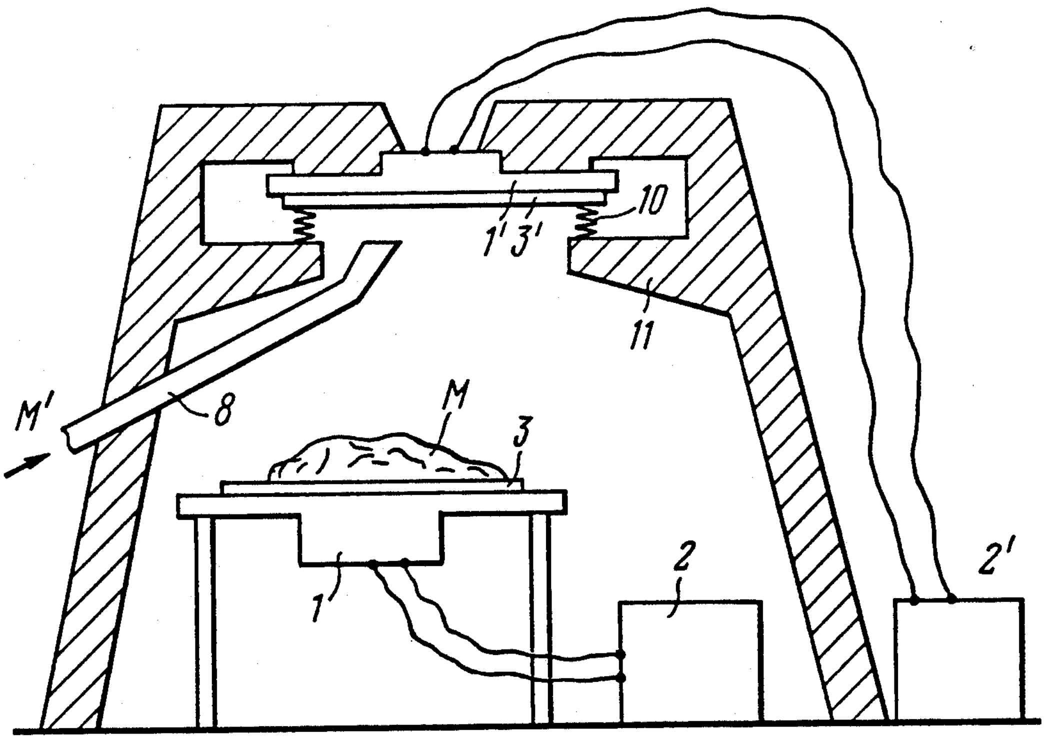
FIG. 7 illustrates another embodiment of an apparatus according to the invention.

The apparatus illustrated in FIG. 7 also has pairs of radiators 1, 1', sources 2, 2' and plate elements 3, 3' but they are arranged opposite each other. The plate element 3' has return springs 10 installed on supports 11. This version of the apparatus provides for intensive crushing of material M and its mixing with material M' which latter may also be crushed.

In all the embodiments of the apparatus for carrying out of the disclosed method the plate element 3 shall be of a minimum thickness for the strength requirements.

Obviously, other embodiments of the apparatus for carrying out the disclosed method can be envisaged, for example, a combination of high acceleration with thermal, chemical an other effects.

Industrial Applicability

The invention can be employed in various branches of industry for drying, moistening, heat exchange (heating or cooling) of solid and liquid materials, e.g. in food, medical-and-pharmaceutical industries, in the production of plastics, construction materials, in the chemical industry, actually in all fields where intensive treatment of materials is required. It can also be used for low-temperature sterilization of various materials. Moreover it can be used for impregnation, disintegration, and for removal of ice and other deposits from various surfaces.

I claim:

1. A method for treating liquid and solid material by acceleration by mechanical energy applied to the material to be treated which comprises: placing a material to be treated in contact with a first surface of a plate element formed from an electric conducting material, the plate element having at least one degree of freedom in a present direction of the acceleration; and contacting a second surface of the plate element, opposite to the first surface of the plate element, with a radiator; and applying an electromagnetic pulse to the radiator, whereby the plate element is accelerated in the preset direction.

2. A method of claim 1 wherein the material to be treated is water whose flow is directed to contact the first surface of the plate element and the electromagnetic pulse is emitted in a continuous mode.

3. A method of claim 1 wherein the material to be treated is a biological material to be sterilized.

4. A method of claim 3, wherein the biological material is placed into a container installed on one surface of the plate element.

5. A method of claim 1 wherein the first surface of the plate element is contacted with concurrent flows of at least two materials to be mixed.

6. A method according to any one of claims 1 through 5 wherein the leading edge of the electromagnetic pulse is determined by a pulse rise time equal to 10% to 20% of the pulse duration.

7. An apparatus for carrying out the method of claim 1 comprising: a source (2) of electromagnetic pulses; a radiator (1) in electrical communication with its source of electromagnetic pulses; a plate element (3) arranged with at least one degree of freedom in a preset direction, and having a first surface and a second surface, the second surface of the plate element (3) being in physical contact with the radiator (1) of electromagnetic pulses and the first surface, opposite the second surface in the preset direction, is arranged to contact a material to be treated.

8. An apparatus of claim 7 which comprises: at least one additional plate element (3) in physical contact with a corresponding additional radiator (1).

9. An apparatus of claim 7, which further comprises: a reflector (9) set at a distance from the first surface of the plate element (3) and arranged parallel with its first surface to contact the material being treated.

* * * * *